Figure 1:
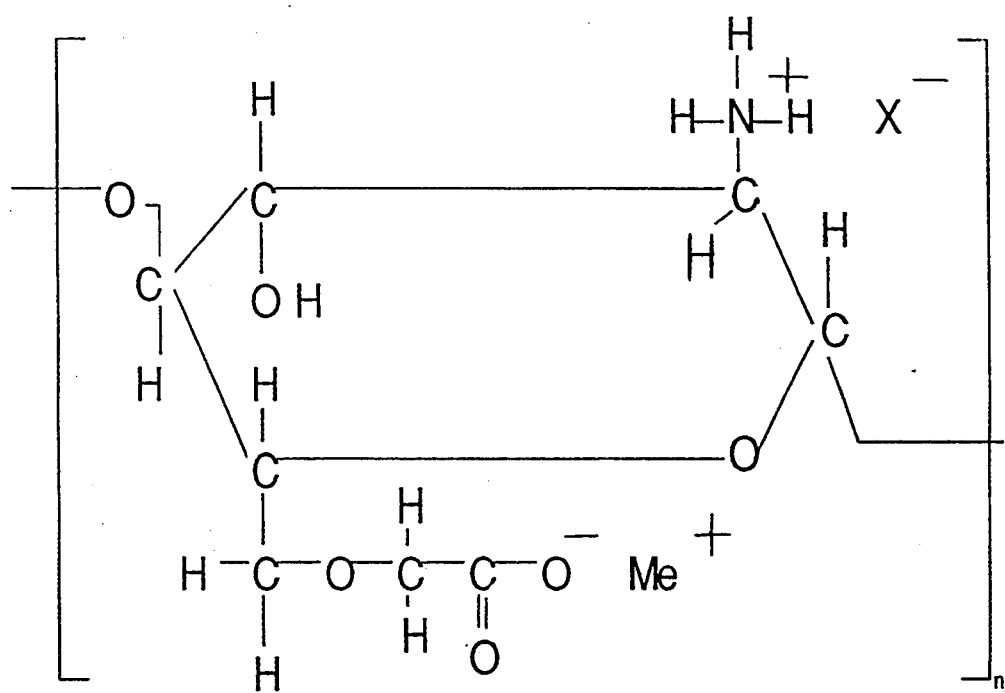

United States Patent [19]

Elson et al.

[11] Patent Number: 5,412,084
[45] Date of Patent: May 2, 1995

[54] N-O-CARBOXYMETHYLCHITOSONIUM CARBOXYLATE SALTS

[75] Inventors: Clive M. Elson; Dennis T. Curran, both of Halifax; Susan E. Henderson, Wellington, all of Canada

[73] Assignee: Nova Chem Limited, Halifax, Canada

[21] Appl. No.: 9,083

[22] Filed: Jan. 26, 1993

Related U.S. Application Data

[63] Continuation of Ser. No. 772,405, Oct. 9, 1991, abandoned.

[51] Int. Cl.[6] .................. C08B 37/08; C07H 5/04; C07H 5/06
[52] U.S. Cl. .................. 536/20; 536/55.2; 536/55.3
[58] Field of Search .................. 536/20, 55.2, 55.3; 514/55

[56] References Cited

U.S. PATENT DOCUMENTS 4,301,067 11/1981 Koshugi .................. 536/20
4,619,995 10/1986 Hayes .................. 536/20

FOREIGN PATENT DOCUMENTS 28126 6/1981 European Pat. Off. .

Primary Examiner—John W. Rollins
Assistant Examiner—Everett White
Attorney, Agent, or Firm—D. Ron Morrison

[57] ABSTRACT

New derivatives of carboxymethyl chitosan are disclosed, which are designated as N,O-Carboxymethylchitosonium carboxylates. The derivatives are ammonium salts made by acidifying a substantially neutral suspension of solid N,O-carboxymethyl chitosan in a diluent with an aqueous solution of the carboxylic acid. The carboxylic acid substitutes on the primary amine sites of the N,O-carboxymethyl chitosan.

23 Claims, 1 Drawing Sheet

N-O-CARBOXYMETHYLCHITOSONIUM CARBOXYLATE SALTS

This application is a continuation of U.S. application Ser. No. 07/772,405, filed 9 Oct. 1991, now abandoned.

This invention relates to novel derivatives of carboxymethyl chitosan, in particular N,O-carboxymethyl chitosan, more particularly to carboxylic acid salts of this material, and to methods of preparing them.

Carboxymethyl chitosan derivatives of chitosan are old in the art, with the N-carboxymethyl derivative and its preparation having been well described, e.g. by Muzzarelli et al, (Carbohydrate Research, 107 (1982), p.p. 199–214) and the O-carboxymethyl derivative and its preparation having being described, e.g. by Nud'ga, Danilov, et al (Jour. Gen. Chemistry U.S.S.R. 1973, 43(12) 2752–6). These two derivatives have carboxymethyl groups substituted exclusively on the amine group or on the hydroxyl groups respectively of unsubstituted chitosan.

In U.S. Pat. No. 4,619,995 of Ernest R. Hayes issued 28 Oct. 1986 there was disclosed the novel carboxymethyl derivative of chitosan having carboxymethyl groups substituted both on the amine group and on the hydroxyl groups of chitosan, with the degree of substitution of carboxymethyl groups per glucosamine monomer unit being less than 1.0; methods for preparation of the N,O-carboxymethyl chitosan derivative (hereinafter usually briefly referred to as NOCC) were also disclosed. This patent also described the process of loosening the coiling and interlocking of chitosan polymer chains in the solid phase by swelling the solid polymer, while it is slurried in an appropriate liquid phase, with sodium hydroxide added to the dispersing liquid as a strong aqueous caustic solution of 25 to 50 percent concentration. Numerous suitable slurrying liquids could be used, including isopropanol, n-butanol, isobutanol, methyl ethyl ketone, toluene, and ethanoltoluene mixtures containing 72 mole percent or more of toluene. They are liquids which do not themselves dissolve nor soften chitosan but do effectively distribute the aqueous caustic solution between the particles of chitosan in the slurry.

In U.S. Pat. No. 4,929,722 issued 29 May 1990 to E. M. Partain and G. L. Brode, there is disclosed a method of "decrystallization" of chitosan in the solid phase while it is dispersed as a slurry in a diluent liquid medium containing (1) an acid that is at least partially water soluble, (2) a polar organic liquid compound that is water soluble but non-solvent for both chitosan and for a desired chitosan derivative, and (3) water in excess of the amount of acid and up to 65 percent of the medium. In Example 1 of that patent, chitosan slurried in isopropanol and water was "decrystallized" with acetic acid, then "causticized" with 50 percent aqueous sodium hydroxide. The "causticized" slurry material was then reacted with monochloroacetic acid, which purportedly would have caused formation of N-carboxymethyl chitosan according to the equation in column 8 line 35 of the patent, but it is acknowledged at column 7 lines 50–53, that the chitosan may have been substituted at other positions. In any event, the product of Example 1 of that patent is not identified by name or structure, nor otherwise defined except, for example, at column 9 lines 56–66, where reference is made to "Covalent chitosan derivatives of the present invention include the products of causticized chitosan and various electrophiles including—sodium chloroacetate or chloroacetic acid—". Thus carboxymethyl chitosan made by that process is there defined simply as a water soluble covalent chitosan derivative, but no indication is given as to whether it is N-carboxymethyl chitosan, O-carboxymethyl chitosan, or NOCC. Furthermore, there is no suggestion for making any derivatives of the covalent material.

It must be noted that, in O-carboxymethyl chitosan, the amine groups are substantially all free of substitution with acyl groups (in contrast with O-carboxymethyl chitin, which has acetyl groups substituent on most of the amine nitrogens), and there are, theoretically, no carboxymethyl group substituents on the amine nitrogens of O-carboxymethyl chitosan. This material thus is practically completely primary amine in structure and might be free to exhibit the basic properties of primary amines, including the possibility of forming salts.

In contrast, O-carboxymethyl chitin has acetyl group substituents on most of the nitrogen atoms in its formula, is therefore more like an amide in structure, and therefore relatively neutral and unlikely to exhibit any basic properties.

Similarly N-carboxymethyl chitosan, having carboxymethyl substituents on most if not all of its nitrogen atoms, has little or no primary amine structure, the carboxymethyl substituents making it essentially a secondary amine. As a secondary amine, it would be expected to have only about one tenth of the basicity, or $pK_b$, of the corresponding primary amine, and may not be expected to form salts.

The N,O-carboxymethyl chitosan, as disclosed in the art, has a degree of polymerization (n), like that of its parent chitosan and its derivatives and addition products, typically in the range from about 500 to about 15,000, most usually in the range from 1,000 to 8,000, and has carboxymethyl substituents on some of its hydroxyl groups (probably most of these on the primary hydroxyl group in the 6 position although some of them could be on the secondary hydroxyl group in the 3 position), and carboxymethyl substituents on some of its nitrogen atoms. As the total degree of substitution is less than 1.0, i.e. there is less than one carboxymethyl substituent per glucosamine monomer unit in the chitosan, and substitution occurs more readily on the hydroxyl oxygen atom than on the amine nitrogen atom, apparently because the amine centres are involved in internal hydrogen bonding within the structure of the chitosan polymer and are not as accessible as the alcoholic side chain for substitution reaction, it is found generally that the ratio of primary amine to secondary amine units in NOCC is about 2:1. Hence with only a small proportion (typically 20%–25%) of the nitrogen atoms in NOCC having carboxymethyl groups thereon and an even smaller proportion (typically 10%–15%) of them having acetyl groups thereon, there are still over half the amine groups that are free, primary amine groups, unsubstituted by acetyl or carboxymethyl groups. Thus NOCC might also be able to exhibit, to a significant degree, the basic properties of a primary amine including the possibility of forming salts comparable to any formed by O-carboxymethyl chitosan.

Although the formation of O-carboxymethylchitosonium carboxylate salts can be hypothesized, nobody appears to have prepared or reported any, and no method has ever been suggested for preparing them. However, it has now unexpectedly been found that N,O-carboxymethyl chitosan can be protonated with numerous carboxylic acids at its unsubstituted (primary) amine sites to form salts analogous to carboxylic acids salts of primary amines, which salts are defined as N,O-carboxymethylchitosonium carboxylates. These materials have unexpected, valuable properties, and are particularly useful, as is disclosed hereinafter.

In the accompanying drawing, FIG. 1 represents the structural formula of the novel monomer unit in a N,O-carboxymethylchitosonium carboxylate polymer chain wherein X represents carboxylate anion, present in a proportion in the range from 0.20 to 0.80, preferably from 0.40 to 0.60, of all chitosan monomer units in the polymer chain, Me represents alkali metal ion, and n represents the degree of polymerization of the polymer.

The invention thus consists in the carboxylate salts of N,O-carboxymethyl chitosan polymer wherein from 20% to 25% of the nitrogen atoms of the N,O-carboxymethyl chitosan in the polymer chain have carboxymethyl substituents thereon. The salts are characterized by having, in their chitosan polymer chain structure, a proportion of monomer units having the formula shown in FIG. 1, wherein X represents a carboxylate anion, present in a proportion in the range from 0.20 to 0.80, preferably from 0.40 to 0.60, of all monomer units in the polymer chain, Me represents alkali metal ion, and n represents the degree of polymerization of the polymer.

The invention further consists in a process for preparation of carboxylate salts of N,O-carboxymethyl chitosans having from 20% to 25% of the nitrogen atoms in their polymer chains with carboxymethyl substituents thereon, which comprises (1) suspending the carboxymethyl chitosan in particulate form in an organic diluent-water mixture which does not dissolve nor render the suspended particles adherent, glutinous, gummy, or sticky, (2) adding 0.20 to 0.80 preferably 0.40 to 0.60 moles of carboxylic acid per mole of carboxymethyl chitosan monomer units in the suspension, said carboxylic acid being dissolved in water, organic solvent for the acid, or a mixture thereof while adjusting the proportion of water in the suspension to maintain the suspended particles separate and discrete and the carboxylic acid in solution, (3) stirring the heterogeneous suspension for substantially one hour at room temperature, (4) separating the solid particles from the suspension, (5) washing the solid particles with anhydrous alcohol to remove residual water, unreacted carboxylic acid, and diluent, and (6) recovering and drying the resulting carboxylate salt.

Preferably the organic diluent-water mixture contains substantially 12% (v/v) or less of water and the organic diluent is acetone, methanol, isopropanol, n-butanol or isobutanol. Furthermore, the proportion of water in the suspension when the acid has been added preferably is adjusted to be in the range of 30% (v/v) or less of the liquid phase, more preferably in the range from 25% to 30%

The invention will be better understood from the ensuing description of examples thereof and of properties and utility of the products.

The following Example 1 illustrates a procedure for preparing the acetate salt of N,O-carboxymethyl chitosan in which the starting material is commercially available chitosan. As mentioned in the literature, chitosan must be swollen, opened up, or "decrystallized", to expose the active sites along the polymer chain in the solid state, to initiate and promote its entrance into chemical reaction. Aqueous media of organic acid and polar organic liquid, particularly acetic acid media, are purported to do this, but are unsuitable for the production of NOCC because of the high proportion of water required in the media (always over 30%) and the ready solubility of NOCC in such aqueous media. When chitosan is swollen with concentrated aqueous caustic in an inert organic liquid medium as taught in the art, NOCC can be formed in the solid state in such media. The resulting NOCC, still swollen by aqueous caustic, in the solid state and in the presence of a liquid organic diluent and a small proportion of water, can then be reacted with sufficient proportions of carboxylic acids in aqueous or aqueous organic solvent solution to neutralize (to pH7) entrapped caustic plus excess of the acid to protonate the unsubstituted amine centers on the NOCC to form salts of the carboxylic acids. The amount of carboxylic acid that is added in excess of that required to neutralize entrapped caustic is generally 0.20–0.080, preferably 0.40 to 0.60 moles acid per mole of NOCC monomer, and the reaction is generally completed by stirring the ingredients for substantially one hour at room temperature then the solid product can be isolated. Commercial chitosan, as generally available and used for this procedure, has a degree of deacetylation of its parent chitin of greater than 80%, preferably 85%–90%.

Example 1

A quantity of 40.0 g of commercial chitosan (viscosity of 1080 cps, 1% solution in 1% acetic acid, Brookfield Viscometer No. 4 spindle, 50 rpm) was slurried in 695 mL isopropanol at room temperature; 131.5 g of 18.161M aqueous sodium hydroxide solution was gradually added to the slurry over a period of 20 minutes, with stirring which was continued for one hour. Next a quantity of 48.0 g of monochloroacetic acid was added with stirring over a 20 minute interval, then the temperature of the mixture was raised to 60 degrees C. and held there for three hours. Thereafter when the mixture had cooled, the solid product was separated by filtration and resuspended in one liter of 70% (v/v) methanol-water for 15 minutes as a wash, then three mL of glacial acetic acid were added and stirring continued for one hour. The solid product was collected by filtration then reslurried in one liter of 80% methanol-water for 15 minutes for a final wash, collected by filtration, and air dried. The white N,O-carboxymethyl chitosonium acetate product weighed 52 g.

A second and preferred method for preparation of N,O-carboxymethylchitosonium carboxylates uses previously prepared and dried powdery NOCC as a starting material, and has been found to be easier to control and quantify. In this procedure, NOCC in solid form is suspended to form a slurry in an organic diluent water mixture to which is slowly added a known amount of carboxylic acid, generally 0.20–0.80, preferably 0.40 to 0.60 moles per mole of NOCC monomer units, the acid being dissolved in an organic diluent or water. Conveniently then, water is added to the diluent-water medium of the slurry to adjust the total water content of the diluent-water medium to 25%–30% (v/v). In some instances a higher proportion of water may be employed to ensure that the carboxylic acid remains in solution. The organic diluent-water mixture and its proportions are selected to ensure that the mixture has minimal solvent action on the NOCC and NOCC salt product, i.e. does not cause the solid reactant or product particles to dissolve, soften, or fuse and stick together.

The following examples 2 to 4 were carried out using commercially available NOCC for the preparation of carboxylate salts with three typical acids forming N,O-carboxymethylchitosonium carboxylates. Commercial NOCC is characterized as a whitish, free-flowing powdery solid that dissolves in water to yield a solution of pH generally in the range of 7.8 to 8.6, which solution is very lubricious, i.e. it feels slippery and considerable quantities of water are required to wash a glass or plastic surface free from NOCC. The degree of substitution (D.S.) of carboxymethyl groups on the chitosan is generally about 0.7 in the commercial product, although it can range from 0.4 to 0.8. Substitution of carboxymethyl groups on the chitosan is predominantly at the oxygen of the primary alcohol group by a ratio of approximately 2:1 over substitution at the amine center. The degree of deacetylation of the amine sites is generally in the range of 85% to 90% in commercial NOCC, i.e. the NOCC is made from chitosan in which the acetyl groups of original chitin have been removed to leave a chitosan having 15% to 10% of the monomer units in the polymer with an acetyl group substituted on the amine nitrogen. Aqueous solutions of 0.5% (w/v) concentration of NOCC have maximum viscosities of a few hundred centipoises in the substantially neutral pH range; NOCC forms a gelatinous, highly hydrated precipitate in such aqueous solutions in the pH range 3–6, whether acidified with carboxylic acids or inorganic acids. The precipitates formed with carboxylic acids are believed to be not carboxymethylchitosonium carboxylates of the present invention. It may be hypothesized that the precipates have hydrogen substituted for the alkali metal on the carboxymethyl group of NOCC, which hydrogen slowly migrates to the primary amine groups and, with the carboxylate anions in the solution, gradually forms carboxymethylchitosonium carboxylate salts which are water soluble, because the precipitates gradually dissolve. However, this would be a laborious, inefficient, and impractical way to form the salts and the herein disclosed heterogeneous reaction methods are preferred, particularly because formation of the salts in the solid state obviates the need for recovering them from the dissolved state.

Example 2—Part A

This example illustrates the preparation of N,O-carboxymethylchitosonium acetate, starting from a supply of NOCC and acetic acid. A quantity of 25.0 g (0.125 mole) of NOCC was slurried in 625 mL of 88% (v/v) isopropanol-water. A quantity of 3.75 g (0.063 moles) glacial acetic acid was dissolved in 710 mL 88% (v/v) isopropanol-water. The acid-containing solution was slowly added to the NOCC slurry with stirring. A quantity of 265 mL of deionized water was then added to the slurry and the stirring was continued for one hour. The solid was separated from the slurry by filtration and the solid product was resuspended in 625 mL of anhydrous isopropanol for 15 minutes. The solid was again recovered by filtration and air dried to yield a whitish salt product, N,O-carboxymethylchitosonium acetate, weighing 24.8 g. The salt was a free-flowing powder soluble in water at room temperature. With a degree of substitution of sodium carboxymethyl groups per monomer unit in the reactant polymer of 0.7, the product salt was determined to have a degree of substitution of acetic acid groups per monomer unit of substantially 0.55. The pH of a 0.1 (w/v) aqueous solution of the salt was in the range 6.7–6.9 and its viscosity measured with a Brookfield Viscometer, Spindle No. 4, 50 rpm, was 290 centipoises.

It must be noted that the yield of solid product is less than theoretical, the solid product weighing less than the solid reactant despite the addition of the carboxylate substituent. More than one factor contributed to this result, the principal ones likely being (a) the loss of low molecular weight fractions of the polymeric reactant and product, which fractions are more readily soluble in the aqueous medium and dissolved out therein, thereby being lost in the liquid phase of the slurry, and (b) the presence of residual sodium acetate impurity in the reactant N,O-carboxymethyl chitosan, which impurity also is water soluble and readily dissolved out of the solid phase by the aqueous liquid phase of the slurry,, with a consequent yield loss.

Example 2—Part B

In a series of parallel reactions carried out as described in Part A of this example, the number of moles of acetic acid added to react with a fixed number of moles (0.01) of NOCC was varied between 0.001 and 0.006. The products of the reactions were dissolved in water to form 0.2% (w/v) aqueous solutions of the products, and the pH and viscosity of the respective solutions measured. The results of the measurements are listed in the following Table 1, beside the proportions of reactants.

TABLE 1

| Moles of NOCC Monomer | Moles of Acetic Acid Added | pH | Viscosity (cps) (*) |
|---|---|---|---|
| 0.01 | 0 | 8.47 | 55 |
| 0.01 | 0.001 | 8.08 | 48 |
| 0.01 | 0.002 | 7.39 | 56 |
| 0.01 | 0.004 | 6.96 | 1462 |
| 0.01 | 0.006 | 6.80 | 2530 |

(*) 0.2% (w/v) aqueous solutions

As can be seen from the data (particularly the pH of the solutions), as the number of moles of acid added to the reaction is increased and once the pH falls below 7, the nature of the NOCC polymer changes, as evidenced by the dramatic increase in the room temperature viscosity of the 0.2% (w/v) solutions. The increase in the viscosity is so great that gels are formed at concentrations of 0.4%–0.5% (w/v) and above.

EXAMPLE 3

This example illustrates the preparation of N,O-carboxymethyl chitosonium pyroglutamate, starting from commercial NOCC. A quantity of 5.0 g of NOCC was slurried in 125 mL of isopropanol. A quantity of 2.26 g DL-pyroglutamic acid (2-pyrrolidone-5-carboxylic acid) was dissolved in 125 mL of 88% (v/v) isopropanol-water with warming. The acid solution was added slowly to the NOCC slurry with stirring. A quantity of 70 mL of deionized water was then added to the mixture and the stirring was continued for 1.5 hr. The solid product was separated from the slurry by filtration and re-suspended in 125 mL of 88% (v/v) isopropanol-water for 15 minutes. The solid product was again separated by filtration and air dried, yielding 4.5 g of whitish free-flowing powdery salt, N,O-carboxymethyl-chitosonium pyroglutamate. The pH of a 0.1% (w/v) aqueous solution of the salt was in the range 6.1–6.3 and its viscosity, measured with a Brookfield Viscometer, Spindle No. 4, 50 rpm, was 81 centipoises.

Example 4

This example illustrates the preparation of N,O-carboxymethylchitosonium glutamate, starting from commercial NOCC. A quantity of 5.0 g of NOCC was slurried in a mixture of 75 mL acetone and 8.3 mL water. A quantity of 2.60 g of glutamic acid was dissolved in 83.3 mL of warm deionized water. The acid solution was added slowly to the NOCC slurry with stirring, and stirring continued. The water content of this particular reaction mixture was 55%; such a high proportion of water was required to hold the glutamic acid in solution. Acetone was used in lieu of isopropanol because, in a 45%/55% mixture of acetone/water, NOCC remains suspended as manageable, discrete, non-gummy, slightly hydrated particles while the glutamic acid remains in solution for reaction with the NOCC. After 1.5 hrs of stirred reaction, the solid in the slurry was separated by filtration, washed with a mixture of 112.5 mL acetone and 12.5 mL water for 15 minutes, and again separated by filtration and air dried. The product salt, N,O-carboxymethylchitosonium glutamate, was a white powdery solid weighing 5.06 grams. The pH of a 0.1% (w/v) aqueous solution of the salt was in the range 5.1–5.3 and its viscosity, measured with a Brookfield Viscometer, Spindle No. 4, 50 rpm, was 20 centipoises.

Example 5–11

This series of examples was carried out using the procedure described above in Example 2, Part A, but substituting for the mole equivalents of acetic acid, mole equivalents of the series of carboxylic acids: salicylic, lactic, lauric, benzoic, para-amino benzoic, propionic, and citric, respectively for Examples 5–11. In each case the product salt was a powdery solid, soluble in water at room temperature to give 0.1% (w/v) solutions less lubricious than parent NOCC solutions and 0.5% (w/v) solutions that have a pH of less than 7 and are non-pourable, clear, colorless gels. Some additional properties for each of these salts are listed in Table 2 below, opposite their respective example number, including the pKa(s) of the parent acid, the pH of a 0.1% concentration (w/v) aqueous solution of the salt, and the viscosity in centipoises of such solution measured with a Brookfield Viscometer, Spindle No. 4, 50 rpm. Glutamic and citric acids, being di- and tri-carboxylic acids respectively, have corresponding multiple pKa(s). For comparison, the corresponding data for the salts of Examples 2A, 3, and 4 are included in Table 2.

TABLE 2

| Ex. No. | NOCC-Salt | pKa(s) of Parent Acid | pH** | Viscosity ***(cps) |
|---|---|---|---|---|
| 2A | Acetate | 4.75 | 6.7–6.9 | 290 |
| 3 | Pyroglutamate | — | 6.1–6.3 | 81 |
| 4 | Glutamate | 2.19 9.67 | 5.1–5.3 | 20 |
| 5 | Salicylate | 2.97 | 6.0–6.2 | 24 |
| 6 | Lactate | 3.86 | 6.7–6.9 | 350 |
| 7 | Laurate | * | 6.8–6.9 | 30 |
| 8 | Benzoate | 4.19 | 6.5–6.7 | 150 |
| 9 | Para-amino benzoate | 4.92 | 6.8–7.0 | 274 |
| 10 | Propionate | 4.87 | 6.9–7.1 | 300 |
| 11 | Citrate | 3.08 4.74 5.40 | 5.2–5.4 | 18 |

*water insoluble
**0.1% (w/v) solution
***0.1% (w/v) solution, Brookfield Viscometer, Spindle No. 4, 50 rpm
****cf: Aqueous NOCC solutions have a pH of 7.8–8.6

The data of Table 2 confirm the acid-base nature of the NOCC-salts formation reaction, not only by the lower pH values of the NOCC-salt solutions compared to NOCC solutions (7.8–8.6) but also by the excellent correspondence (other than an apparent anomaly for the lactate) between the pH of the NOCC-salt solutions and the pKa values of parent carboxylic acids when the data are plotted graphically. Noting the structural formula for the compounds, as illustrated in FIG. 1, it can be observed that the protonated amine center imparts a weak acid character to the compound and, from a comparison of the titration curves of the compounds and of NOCC when titrated with sodium hydroxide to pH inflection point generally between 10 and 11, usually about 10.2, a degree of substitution of carboxylic acid on the amine centers of the carboxymethylchitosonium carboxylate salts can be established. The calculation requires a series of iterative determinations. As the titration of the NOCC carboxylate salts proceeds, it is noted that lubricity returns to the solution once the pH rises above 7. From such a calculation, NOCC acetate salt is found to have a degree of substitution of 0.55, i.e. the salt has an average of 0.55 mole of carboxylic acid group substituents per mole of monomer units in the carboxymethyl chitosan polymer. In general, the degree of substitution of the carboxylic acids in the carboxymethylchitosonium carboxylates is found to be in the range from 0.5 to 0.7.

Specifically for a quantity of NOCC acetate derivative made by the method described in Example 2A, with a degree of substitution of 0.7 sodium carboxymethyl groups plus 0.55 acetic acid groups per monomer, the percentage sodium in the NOCC-acetate was calculated by the foregoing iterative calculations to be 6.47%. The experimental determination for the ash of this derivative was 0.80%. Conversion of the percent ash (as sodium oxide) to percent sodium yielded a value of 6.53%, in excellent agreement with the foregoing calculated value of 6.47% and further confirming the proposed structure of the NOCC salts.

The foregoing agreement between the calculated and experimental sodium contents of NOCC supports the hypothesis that the carboxymethyl group is retained during the salt formation reaction. The retention of the carboxymethyl group is also supported by the pH values of the NOCC salts (Table 2 herein) as, if these carboxymethyl groups were lost during the formation reaction, the final product would be identical to chitosan-carboxylate salts which have considerably lower pH values. (Vide: Partain and Brode, U.S. Pat. No. 4,929,722, columns 13–14, Table 1, giving a list of pKa values for such compounds, all in the range from 2 to 5.

Another characteristic of NOCC-carboxylate salts is the dramatic loss of viscosity upon the addition of small amounts of inorganic salts. Most NOCC-carboxylate salts yield a gel when dissolved in water at 0.5% (w/v) concentration; if a few crystals of sodium chloride are sprinkled onto the gel and stirred in, the gel decomposes leaving a thin, cloudy solution within a minute. The addition of sodium hydroxide also causes this effect once the pH of the NOCC-carboxylate salt solution is raised above 7. The addition of acid also causes the loss of viscosity to occur once a pH of 5 has been reached.

Numerous applications of the compounds for various purposes suggest themselves to those skilled in the art, when their properties and the structures of the compounds and their solutions are considered. The pH of the compounds and their solutions approaches neutrality (typically the pH range 5–7). The polyglucosamine skeleton of the polymer is related to the structure of human hyaluronic acid which is a muco-polysaccharide of alternating D-glucuronic acid and N-acetyl-D-glucosomine units. The compounds are white and form clear, colourless, odourless solutions of high viscosities at low concentrations (0.5% solutions are gels). Such materials are useful in the formulation of numerous cosmetics.

For example of such use, a hand-care cream was prepared. A quantity of 0.5 g NOCC-acetate was dissolved in 16 mL of rose water plus 73.4 mL of deionized water; the solution was heated to 65 degrees C. and stirred vigorously as 5.9 g of Aloe Vera (trademark) gel, 2.2 g of glycerin, 1.8 g sorbitol, and 0.15 g lanolin were added. On completion of the additions and stirring, the mixture was cooled to yield a white moisturizing skin cream. The cream was evaluated by a group containing young and mature volunteers who found it to approximate commercial skin care products in its effect, "feel", and ease of absorption. When portions of the cream were placed in a desiccator along with samples from three commercial formulations from the marketplace and their weights monitored with time, it was found that the NOCC-acetate based cream lost moisture at a rate close and comparable to two of the commercial products and at a much lower rate than the third product. One of the better performing moisturizing skin creams in the desiccation test was priced at the high end of the retail range and contained a significant proportion of oils (15.9% mineral oil and 0.6% (w/w) lanolin).

The compound para-aminobenzoic acid (PABA) has been incorporated in sunscreen formulations for a number of years. The NOCC-para-aminobenzoate salt provides cosmetic formulators with a compound that will not only absorb ultraviolet radiation, and thereby protect the underlying skin, but will also thicken the formulation to the desired consistency. The ultra-violet spectrum of 1 millimole NOCC-PABA salt in one liter aqueous solution shows a broad absorption centered at 265 nm with an extinction coefficient of 380 reciprocal mole centimeters.

Numerous modifications can be made in the specific expedients described herein without departing from the invention, the scope of which is defined in the following claims.

What is claimed is:

1. The carboxylate salts of N,O-carboxymethyl chitosan polymer wherein from 20% to 25% of the nitrogen atoms of the N,O-carboxymethyl chitosan in the polymer chain have carboxymethyl substituents thereon, which salts are N,O-carboxymethylchitosonium carboxylates.

2. The carboxylate salts as claimed in claim 1, wherein a proportion of monomer units in the polymer chain have the structural formula

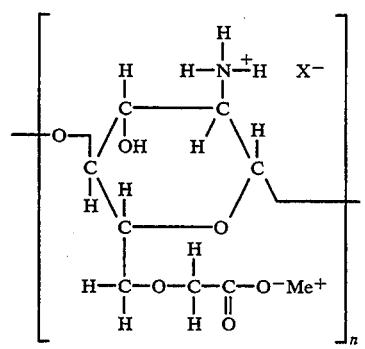

wherein X represents a carboxylate ion, present in a proportion in the range from 0.20 to 0.80 of all monomer units in the polymer chain, Me represents alkali metal ion, and n represents the degree of polymerization of the polymer.

3. The carboxylate salts as claimed in claim 2, wherein the said range is from 0.40 to 0.60.

4. The carboxylate salt as claimed in claim 3, which is N,O-carboxymethylchitosonium acetate.

5. N,O-carboxymethylchitosonium acetate as claimed in claim 4 having a degree of substitution of acetic acid groups per monomer unit of substantially 0.55.

6. The carboxylate salt as claimed in claim 3, which is N,O-carboxymethylchitosonium pyroglutamate.

7. The carboxylate salt as claimed in claim 3 which is N,O-carboxymethylchitosonium glutamate.

8. The carboxylate salt as claimed in claim 3 which is N,O-carboxymethylchitosonium para-amino benzoate.

9. A process for the preparation of N,O-carboxymethylchitosonium carboxylate salts from N,O-carboxymethyl chitosans having from 20% to 25% of the nitrogen atoms in their polymer chains with carboxymethyl substituents thereon, which comprises:

(1) suspending the carboxymethyl chitosan in particulate form in an organic diluent-water mixture which does not dissolve nor render the suspended particles adherent, glutinous, gummy, or sticky, (2) lowering the pH of the suspension below 7 by adding 0.20 to 0.80 moles of carboxylic acid per mole of carboxymethyl chitosan monomer units in the suspension, said carboxylic acid being dissolved in water, organic solvent for the acid, or a mixture thereof while adjusting the proportion of water in the suspension to maintain the suspended particles separate and discrete and the carboxylic acid in solution, (3) stirring the heterogeneous suspension for substantially one hour at room temperature, (4) separating the solid particles from the suspension, (5) washing the solid particles with anhydrous alcohol to remove residual water, unreacted carboxylic acid, and diluent, and (6) recovering and drying the resulting N,O,-carboxymethylchitosonium carboxylate salt.

10. A process as claimed in claim 9 in which the amount of carboxylic acid added to the suspension is in the range from 0.40 to 0.60 moles per mole of said monomer units and lowers the pH thereof below 7.

11. A process as claimed in claim 10 in which the pH is lowered to the range from 5.1 to 6.9.

12. A process as claimed in claim 11 in which N,O-carboxymethyl chitosan is suspended in a mixture of isopropanol and water.

13. A process as claimed in claim 12 wherein said mixture of isopropanol and water contains substantially 12% (v/v) of water.

14. A process as claimed in claim 13 in which glacial acetic acid dissolved in a mixture of isopropanol and water is added to the suspension as the carboxylic acid to form N,O-carboxymethylchitosonium acetate as the salt.

15. A process as claimed in claim 14 wherein the proportion of water in the suspension on addition of the glacial acetic acid mixture is in the range from 25% to 30% (v/v).

16. A process as claimed in claim 13 in which DL-pyroglutamic acid dissolved in a mixture of isopropanol and water is added to the suspension as the carboxylic acid to form N,O-carboxymethylchitosonium pyroglutamate as the salt.

17. A process as claimed in claim 16 wherein the mixture of isopropanol and water contains substantially 12% (v/v) of water.

18. A process as claimed in claim 17 wherein the proportion of water in the suspension on addition of the DL glutamic acid mixture is from 25% to 35% (v/v).

19. A process as claimed in claim 9 in which N,O-carboxymethyl chitosan is suspended in a mixture of acetone and water, glutamic acid is dissolved in warm water and the solution thereof is added to the suspension to form N,O-carboxymethylchitosonium glutamate.

20. A process as claimed in claim 19 in which the mixture of acetone and water contains substantially 10% (v/v) of water and the proportion of water in the suspension on addition of the glutamic acid solution is substantially 55% (v/v).

21. A process as claimed in claim 9, in which the organic diluent is acetone, methanol, isopropanol, n-butanol, or isobutanol.

22. A process as claimed in claim 21 wherein the organic diluent water mixture contains substantially 12% (v/v) of water, and the proportion of water in the suspension on addition of the solution of carboxylic acid thereto is adjusted to the range from 25% to 30% (v/v).

23. A process as claimed in claim 22, in which the amount of carboxylic acid added to the suspension is in the range form 0.40 to 0.60 moles per mole of said monomer units and lowers the pH thereof to the range from 5.1 to 6.9.

* * * * *